(12) United States Patent
Triplett et al.

(10) Patent No.: US 8,357,127 B2
(45) Date of Patent: Jan. 22, 2013

(54) PRE-MOLDED BIFURCATION INSERT

(75) Inventors: Daniel J. Triplett, Providence, UT (US); Robert Weintraub, Draper, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/974,874

(22) Filed: Dec. 21, 2010

(65) Prior Publication Data

US 2011/0098680 A1    Apr. 28, 2011

Related U.S. Application Data

(63) Continuation of application No. 10/670,625, filed on Sep. 25, 2003, now Pat. No. 7,896,853.

(51) Int. Cl.
*A61M 25/00* (2006.01)
(52) U.S. Cl. .................................. 604/284; 604/523
(58) Field of Classification Search ............ 604/80, 604/81, 85, 284, 523, 533–539; 623/1.11
See application file for complete search history.

(56) References Cited

U.S. PATENT DOCUMENTS

| | | |
|---|---|---|
| 883,583 A | 3/1908 | Stallsmith |
| 1,696,018 A | 12/1928 | Scheliberg |
| 2,230,218 A | 2/1941 | Asche |
| 3,256,885 A | 6/1966 | Higgins et al. |
| 3,520,298 A | 7/1970 | Lange |
| 3,610,226 A | 10/1971 | Albisser et al. |
| 3,670,729 A | 6/1972 | Bennett et al. |
| 3,812,851 A | 5/1974 | Rodriguez |
| 3,827,434 A | 8/1974 | Thompson et al. |
| 3,848,592 A | 11/1974 | Willock |
| 4,016,879 A | 4/1977 | Mellor |
| 4,037,599 A | 7/1977 | Raulerson |
| 4,073,297 A | 2/1978 | Kopp et al. |
| 4,098,275 A | 7/1978 | Consalvo |
| 4,099,528 A | 7/1978 | Sorenson et al. |
| 4,253,463 A | 3/1981 | Kim |
| D272,651 S | 2/1984 | Mahurkar |
| 4,493,696 A | 1/1985 | Uldall et al. |
| 4,619,643 A | 10/1986 | Bai |
| 4,670,009 A | 6/1987 | Bullock |
| 4,682,978 A | 7/1987 | Martin et al. |
| 4,895,561 A | 1/1990 | Mahurkar |

(Continued)

FOREIGN PATENT DOCUMENTS

| | | |
|---|---|---|
| EP | 0616817 A1 | 9/1994 |
| WO | 02064202 | 8/2002 |

OTHER PUBLICATIONS

PCT/US2004/027876 filed Aug. 27, 2004 Preliminary Report on Patentability dated Mar. 27, 2006.

(Continued)

*Primary Examiner* — Nicholas Lucchesi
*Assistant Examiner* — Gerald Landry, II
(74) *Attorney, Agent, or Firm* — Rutan & Tucker, LLP

(57) ABSTRACT

A catheter assembly including a coaxial catheter and insert, and method of making. The catheter assembly includes a coaxial catheter, an insert, and a hub. The coaxial catheter includes an inner lumen and an outer lumen. The insert includes first and second passageways, the first passageway defined from a first opening on a distal end of the insert to a second opening on a proximal end of the insert, the second passageway branching from the first passageway to a third opening. A portion of the insert distal end is received in a proximal opening of the outer lumen, and a proximal section of the inner lumen extends through the first passageway. The hub is molded over the insert and a proximal section of the outer lumen.

15 Claims, 3 Drawing Sheets

U.S. PATENT DOCUMENTS

| | | | | |
|---|---|---|---|---|
| 4,931,049 A | * | 6/1990 | Klimas | 604/165.01 |
| 5,053,004 A | * | 10/1991 | Markel et al. | 604/43 |
| 5,129,887 A | | 7/1992 | Euteneuer et al. | |
| 5,167,623 A | | 12/1992 | Cianci et al. | |
| 5,207,648 A | | 5/1993 | Gross | |
| 5,250,041 A | * | 10/1993 | Folden et al. | 604/284 |
| 5,309,906 A | | 5/1994 | LaBombard | |
| 5,350,358 A | | 9/1994 | Martin | |
| 5,395,316 A | | 3/1995 | Martin et al. | |
| 5,395,352 A | | 3/1995 | Penny | |
| 5,395,379 A | * | 3/1995 | Deutchman et al. | 606/123 |
| 5,409,455 A | | 4/1995 | Belden | |
| 5,478,331 A | | 12/1995 | Heflin et al. | |
| 5,599,327 A | | 2/1997 | Sugahara et al. | |
| 5,683,640 A | | 11/1997 | Miller et al. | |
| 5,718,678 A | | 2/1998 | Fleming, III | |
| 5,820,612 A | | 10/1998 | Berg | |
| 5,976,103 A | | 11/1999 | Martin | |
| 6,503,244 B2 | | 1/2003 | Hayman | |
| 6,858,019 B2 | | 2/2005 | McGuckin, Jr. et al. | |
| 6,964,671 B2 | | 11/2005 | Cheng et al. | |
| 6,969,379 B1 | * | 11/2005 | Aboul-Hosn et al. | 604/507 |
| 2001/0012927 A1 | | 8/2001 | Mauch | |
| 2002/0038114 A1 | * | 3/2002 | Segura | 604/533 |
| 2003/0004525 A1 | | 1/2003 | Cheng et al. | |
| 2003/0018308 A1 | | 1/2003 | Tsai | |
| 2004/0181209 A1 | | 9/2004 | Gross | |
| 2005/0059958 A1 | * | 3/2005 | Lessard et al. | 604/533 |
| 2005/0070878 A1 | | 3/2005 | Triplett et al. | |
| 2006/0276773 A1 | * | 12/2006 | Wilson et al. | 604/523 |
| 2009/0143767 A1 | | 6/2009 | Fentress et al. | |
| 2009/0157052 A1 | | 6/2009 | Verbitsky et al. | |

OTHER PUBLICATIONS

PCT/US2004/027876 filed Aug. 27, 2004 Search Report dated Jan. 26, 2005.

PCT/US2004/027876 filed Aug. 27, 2004 Written Opinion dated Mar. 25, 2006.

U.S. Appl. No. 10/670,625, filed Sep. 25, 2003 Notice of Allowance dated Sep. 30, 2010.

U.S. Appl. No. 10/670,625, filed Sep. 25, 2003 Non-Final Office Action dated Feb. 5, 2007.

U.S. Appl. No. 10/670,625, filed Sep. 25, 2003 Non-Final Office Action dated Jan. 8, 2010.

U.S. Appl. No. 10/670,625, filed Sep. 25, 2003 Non-Final Office Action dated Jun. 23, 2010.

U.S. Appl. No. 10/670,625, filed Sep. 25, 2003 Non-Final Office Action dated Jun. 5, 2009.

* cited by examiner

PRE-MOLDED BIFURCATION INSERT

PRIORITY

This application is a continuation of U.S. patent application Ser. No. 10/670,625, filed Sep. 25, 2003, now U.S. Pat. No. 7,896,853, which is incorporated by reference in its entirety into this application.

BACKGROUND OF THE INVENTION

Coaxial catheters are well-known in the art, being used for applications such as hemodialysis, where separate lumens are necessary to simultaneously remove blood from and return treated blood to a patient. Examples of coaxial catheters for use in hemodialysis treatments can be found in U.S. Pat. No. 5,976,103 to Martin. Such coaxial catheters, generally comprised of one or more inner catheters disposed within an outer catheter, are conventionally connected to extension tubing for the purpose of attachment to a dialysis or other treatment device.

This is generally accomplished by molding a hub over the proximal end of the catheter, which transforms the coaxial configuration of the lumens to a side-by-side configuration so that the extension tubing will lay flat against a patient's skin. The extension tubing is then connected to the hub post-processing via a barbed fitting or the equivalent as shown in U.S. Pat. No. 5,053,004 to Markel et al. The hub overmolding process is typically conducted after first inserting a cylindrical pin into an innermost catheter and C-shaped pins into the other catheter(s). Once the molding process is complete, the pins are removed and separate channels are created for the extension tubing.

There are drawbacks, however, to the above-described standard method. First, use of a post-processing connection system for the extension tubing as opposed to overmolding the hub with the extension tubing in place, provides a much weaker connection and one that can become prone to detachment with higher flow rates. Second, use of C-shape rods in the overmolding process can result in flow disturbances and inefficiencies in a functioning catheter, as well as the formation of bubbles, which causes turbulent flow.

For these and other reasons, it would be advantageous to provide a single bifurcation insert for connection to both the catheter and extension tubing prior to a hub overmolding process to provide a complete product that avoids the common drawbacks associated with the standard manufacturing methods of a multi-lumen catheter with respect to a proximal hub for attachment thereto.

BRIEF SUMMARY OF THE INVENTION

Accordingly, a primary object of the present invention is to provide a single bifurcation insert for coaxial catheters, which itself becomes a component of the multi-lumen catheter system. It is another object of the present invention to provide a connection system for extension tubing, which does not detach from the hub under the presence of high flow rates. It is still another object of the present invention to provide a pre-defined fluid path for the lumens of a coaxial catheter that will enable seamless fluid flow between the extension tubing and the respective catheter lumens. It is yet another object of the present invention to provide an efficient and cost-effective method of attaching extension tubing to catheters. Various other objectives and advantages of the present invention will become apparent to those skilled in the art as more detailed description is set forth below.

In accordance with the present invention, several embodiments are described, which may be improvements to bifurcation assembly methods or may be novel hub embodiments heretofore undisclosed. As used herein, the term "venous" denotes the catheter, extension tubing or side of the insert/assembly through which cleansed blood is infused to a patient, while the term "arterial" denotes the catheter, extension tubing, or side of the insert/assembly through which blood to be cleaned is withdrawn from the patent.

The present invention is directed to a bifurcation insert for coaxial catheters as well as a catheter assembly including a bifurcation insert. The bifurcation insert has a distal opening and two proximal openings, one each for the venous and arterial sides. Within the bifurcation insert is two passageways, a first extending from the distal opening to the venous side opening and the second extending from the first passageway to the arterial side opening. At the distal opening and arterial side opening, an outer wall is tapered, resulting in a shoulder so that placement within the outer lumen and first extension tube respectively is facilitated.

The catheter assembly is constructed by placing the bifurcation insert within a proximal end of an outer lumen of a coaxial catheter such that an outer wall of the outer lumen abuts the shoulder at the distal end of the insert. A first extension tube is positioned over the arterial side opening and an outer wall thereof abuts a shoulder adjacent the opening. A second extension tube is positioned in close proximity to an inner lumen, which itself is positioned through the outer lumen of the coaxial catheter and a first passageway of the bifurcation insert, exiting the venous side proximal opening. Pins are placed through the extension tubes and into the arterial side opening and inner lumen, respectively. A hub is overmolded around the assembled parts, locking in place the parts with respect to one another and creating a sealed assembly, after which the pins are removed.

A more complete understanding of the bifurcation insert of the present invention will be afforded to those skilled in the art, as well as a realization of additional advantages and objects thereof, by a consideration of the following detailed description of the preferred embodiments. Reference will be made to the appended sheets of drawings that will first be described briefly.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention satisfies the need for a bifurcation insert for coaxial catheters as an integral component of a multi-lumen catheter system, as well as the need for a reliable, efficient and uniform method of connecting a coaxial catheter to extension tubing. Although the bifurcation insert is described below in connection with a dual-lumen coaxial catheter, it is contemplated that the bifurcation insert could have other applications as well where there is a need to connect passageways together. Further, while a preferred material for the bifurcation insert according to the present invention is plastic, there are many other possible materials that could be utilized that would be within the scope of the present invention, such as stainless steel, titanium, nitinol and epoxy, to name a few. Moreover, while it is contemplated that the bifurcation insert would be formed by a molding process, other methods of fabricating the insert are also possible, such as traditional machining and sintering.

Figure 1:
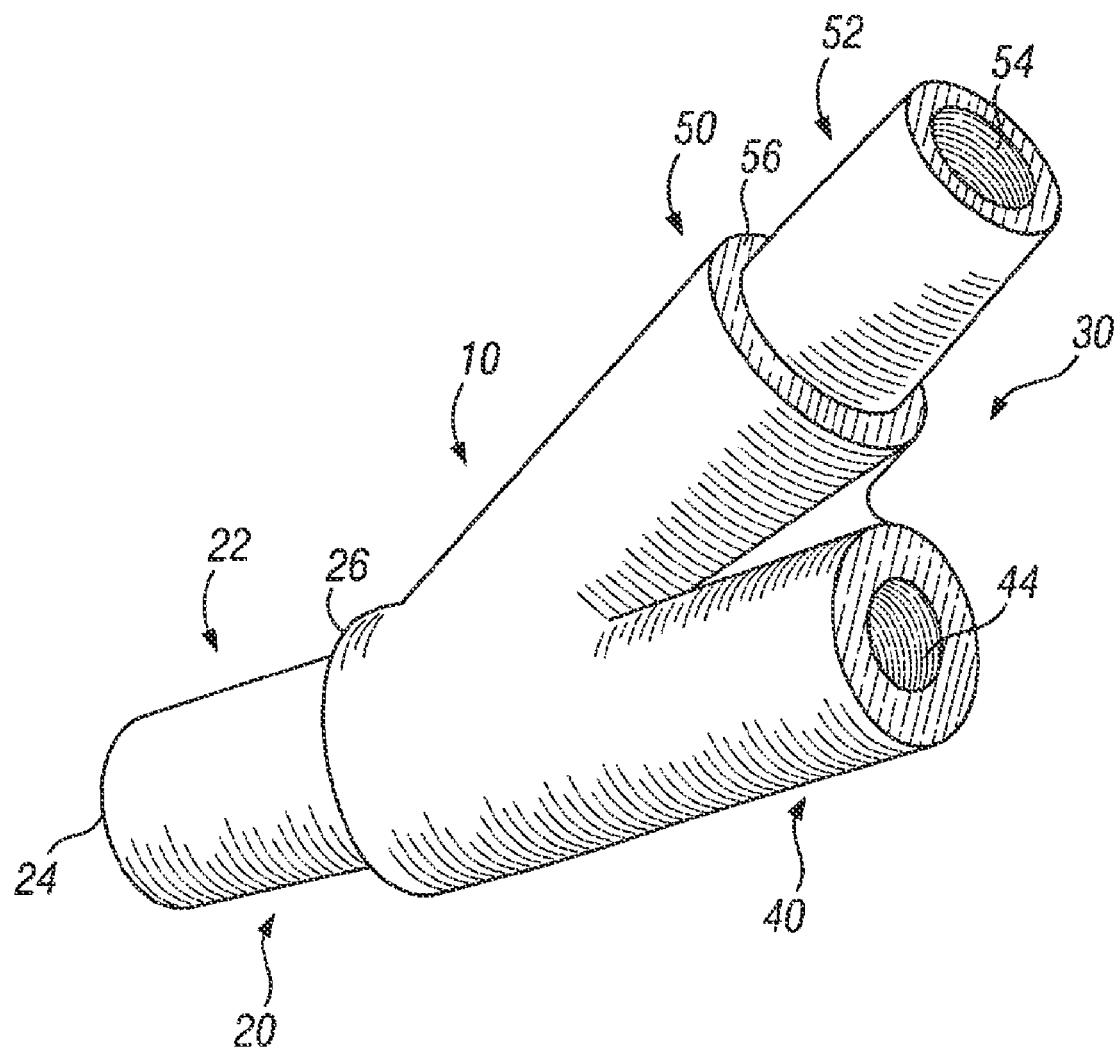
FIG. 1 is a side perspective view of a bifurcation insert according to the present invention.
Figure 2:
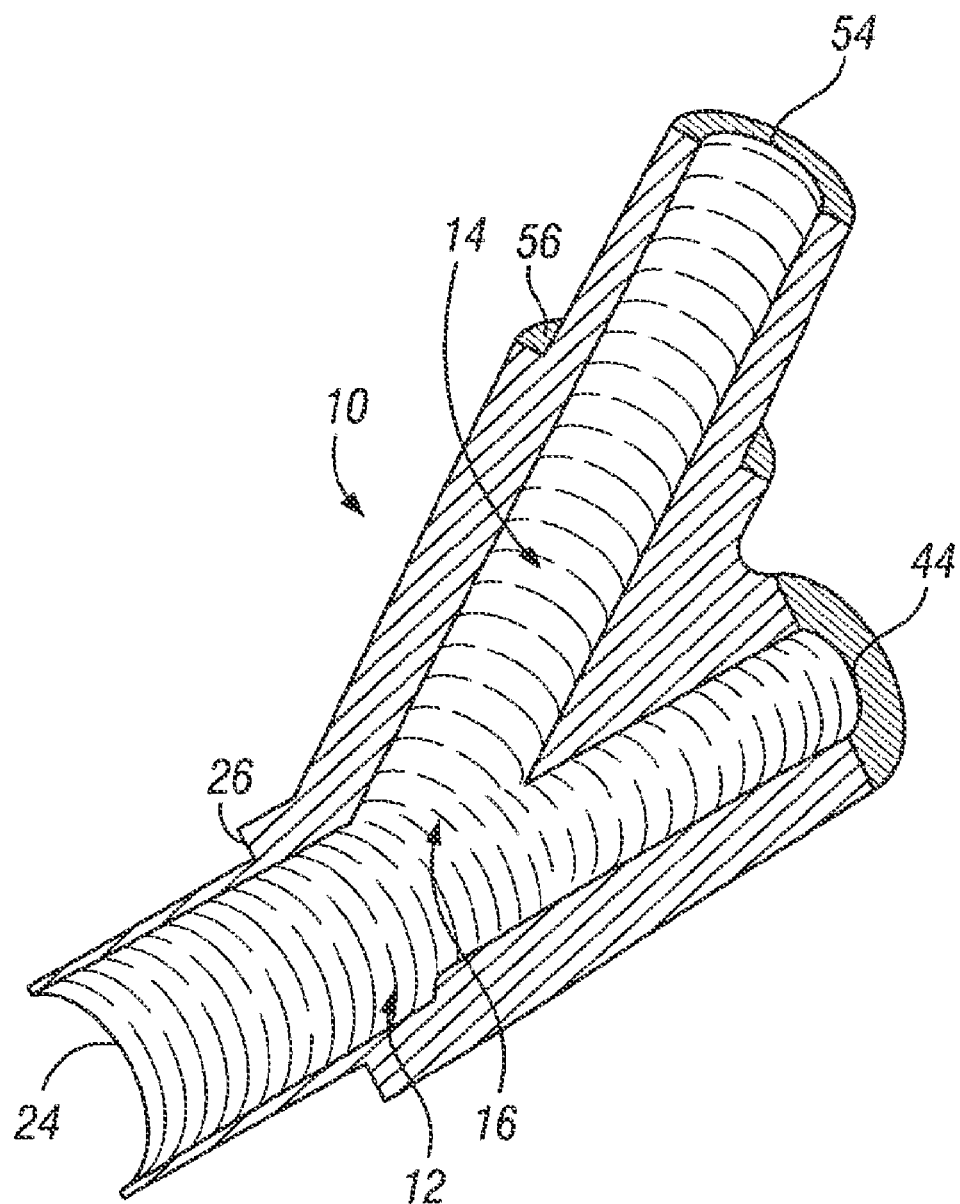
FIG. 2 is a cross-sectional view of the bifurcation insert of FIG. 1.

Referring now to FIG. 1, a bifurcation insert 10 is illustrated, having a distal end 20 and a proximal end 30. The distal end 20 has a tapered portion 22, containing a shoulder 26 and a distal opening 24, the shoulder 26 being configured for abutment with a wall of an outer lumen of a coaxial catheter arrangement as explained below in connection with FIG. 3. The proximal end 30 opens in two locations, having a venous side 40 and an arterial side 50. The venous side 40 of the bifurcation insert 10 extends directly from the distal end 20, forming a substantially straight passageway as shown in FIG. 2. The venous side 40 has an opening 44 that is configured to accommodate an inner catheter of a coaxial catheter arrangement. The arterial side 50 extends at an angle with respect to the distal end 20 and similarly has a tapered portion 52 and a shoulder 56, along with an opening 54. The tapered portion 52 is configured for receiving an extension tube, wherein an outside wall of the tube abuts shoulder 56.

The cross-sectional view of FIG. 2 illustrates the passageways of the bifurcation insert of FIG. 1. From the distal opening 24, a first passageway 12 extends to the venous side opening 44. A second passageway 14 extends from the first passageway 12 at location 16 to the arterial side opening 54. Although location 16 is shown as being closer the distal end 20 than the proximal end 30, it is also possible that location 16 would be closer to the proximal end 30 or that location 16 would be midway between the two ends 20, 30.

Figure 3:
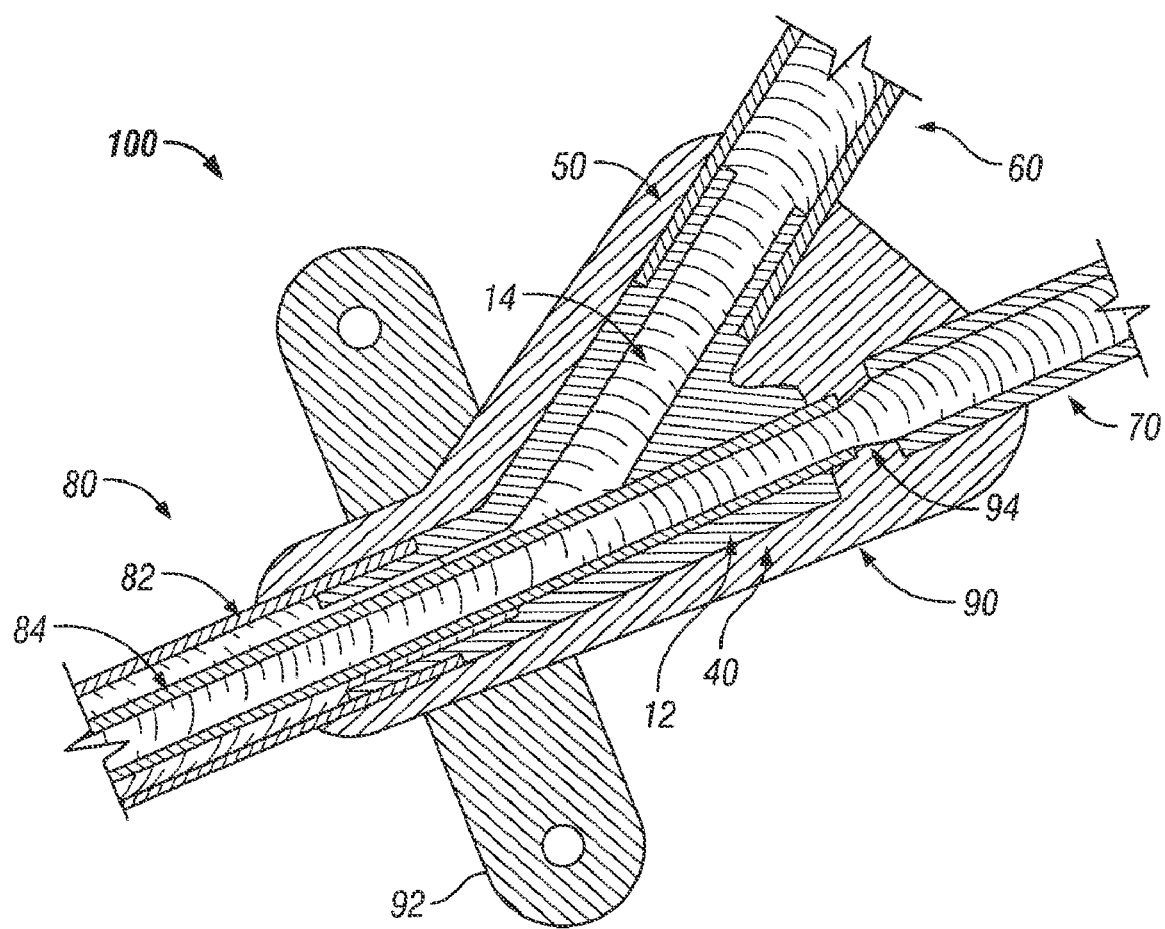
FIG. 3 is a cross-sectional view of an assembled catheter system with an integral bifurcation insert.

Referring now to FIG. 3, a catheter assembly according to the present invention is illustrated in cross-section. The catheter assembly 100 includes the bifurcation insert 10, a coaxial catheter 80, extension tubes 60, 70 and a hub 90. The coaxial catheter 80 contains an inner lumen 84 within an outer lumen 82. The outer lumen 82 is in fluid communication, via the bifurcation insert 10, with a first extension tube 60, while the inner lumen 84 is in fluid communication with a second extension tube 70. The catheter assembly is constructed by inserting the distal end 20 of the bifurcation insert 10 into a proximal end of the outer lumen 82 so that the shoulder 26 abuts an outer wall thereof. The inner lumen 84, which in this example is longer in length than the outer lumen 82, is received within the first passageway 12, entering through the distal opening 24 and exiting the venous side opening 44. The first extension tube 60 is placed over the tapered portion 52 of the arterial side 50 so that a distal end thereof abuts the shoulder 56. The second extension tube is placed in close proximity to a proximal end of the inner lumen 84. Once the insert 10, coaxial catheter 80 and extension tubes 60, 70 have been properly aligned with respect to one another, a first pin (not shown) is placed through the first extension tube 60 and into the arterial side 50 of the bifurcation insert 10 and a second pin (not shown) is placed through the second extension tube 70 and into the inner lumen 84. The pins provide support to the respective lumens and tubes at the proximal end of the assembly during the overmolding process (the distal taper 22 of the bifurcation insert 10 provides support for the outer lumen 82).

Following insertion of the pins, a hub 90 is molded over the assembled parts to lock into place their position with respect to one another. Specifically, the hub 90 extends over the entire bifurcation insert 10 and a portion of the outer lumen 82 and the extension tubes 60, 70. Of course, the distance the hub 90 extends over the outer lumen 82 and extension tubes 60, 70 is variable, the important aspect being that at least a portion thereof be covered so that each are secure and locked into position with respect to one another. Thus, many different possibilities exist with respect to the extent of reach distally and proximally of the hub 90, all of which would be within the scope of the present invention. After the molding process has been completed, the pins are removed from the extension tubes 60, 70. As shown in FIG. 3, a channel 94 is created between the inner lumen 84 and the second extension tube 70 enabling fluid communication therebetween, the channel formed by the second pin during the molding process. While this is one manner in which to establish fluid communication between the inner lumen 84 and the second extension tube 70, certainly other possibilities within the scope of the present invention exist, such as, for example, connecting the inner lumen 84 to the second extension tube 70 prior to molding, abutting the outer walls of the inner lumen 84 to the extension tube 70 prior to molding, inserting the inner lumen 84 within the extension tube 70, etc.

It should be appreciated that the first and second passageways 12, 14 can be constructed having large diameters or smaller diameters, depending on the patient and/or application. In addition, the passageways, 12, 14 can be varying in width along their length and can contain contoured regions to facilitate fluid flow therethrough. Moreover, it may be advantageous to configure the first passageway 12 more narrowly above the junction point 16 so that the inner lumen is tightly fit therein, preventing fluid flow in a direction towards the venous side opening 44, even though said opening would be closed following the molding process. Further, it may be advantageous to configure the arterial side opening 54 greater in diameter than that of the second passageway 14. It should also be appreciated that the angle formed between the first passageway 12 and second passageway 14 can be set at different values, depending on the goals to be attained. For example, a smaller angle may be advantageous in providing optimal comfort for the patient as well as improved flow due to minimized flow redirection. Thus, while an angle of approximately 30° is shown, a preferred range is between approximately 15° and 60°. Of course, both angles smaller than 15° and larger than 60° are equally contemplated and would be within the scope of the present invention.

The present invention has been described above in terms of certain preferred embodiments so that an understanding of the present invention can be conveyed. However, there are many alternative arrangements for a bifurcation insert not specifically described herein but with which the present invention is applicable. Although specific features have been provided, the bifurcation insert of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

What is claimed is:

1. A catheter assembly, comprising:
a coaxial catheter including an inner lumen and an outer lumen;
an insert, including first and second passageways, coupled to the catheter, the first passageway defined from a first opening on a distal end of the insert to a second opening on a proximal end of the insert, the second passageway branching from the first passageway to a third opening, a portion of the insert distal end received in a proximal opening of the outer lumen, and a proximal section of the inner lumen extending through the first passageway from the first opening through the second opening; and
a hub molded over the insert and a proximal section of the outer lumen.

2. The catheter assembly according to claim 1, the insert further comprising a shoulder near the received portion of the insert distal end, the shoulder abutting a wall of the outer lumen defining the outer lumen proximal opening.

3. The catheter assembly according to claim 1, wherein the received portion of the insert distal end is tapered.

4. The catheter assembly according to claim 1, further comprising a first extension tube in fluid communication with the inner lumen and a second extension tube in fluid communication with the outer lumen.

5. The catheter assembly according to claim 4, wherein the hub is molded over a distal section of both the first and second extension tubes.

6. The catheter assembly according to claim 1, wherein the second passageway forms an angle with the first passageway in the range of approximately 15° to 60°.

7. The catheter assembly according to claim 1, wherein the insert comprises a material selected from the group consisting of plastic, stainless steel, titanium, nitinol and epoxy.

8. The catheter assembly according to claim 1, wherein the hub completely encapsulates the insert.

9. The catheter assembly according to claim 1, the first passageway having a first cross-sectional area from the first opening to the second passageway and a second cross-sectional area from the second passageway to the second opening, the first cross-sectional area larger than the second cross-sectional area.

10. The catheter assembly according to claim 9, wherein the inner lumen proximal section has an outer diameter, and wherein the second cross-sectional area approximates the inner lumen proximal section outer diameter.

11. The catheter assembly according to claim 1, wherein a cross-sectional area of the second passageway is larger at the third opening than along a majority of the length thereof.

12. A method of attaching first and second extension tubes to a coaxial catheter with an inner lumen and an outer lumen, comprising:
providing an insert, including a first passageway defined from a first opening on a distal end of the insert to a second opening on a proximal end of the insert, and a second passageway branching from the first passageway to a third opening;
threading a proximal section of the inner lumen through the first opening, through the first passageway, and through the second opening;
inserting a portion of the insert distal end into a proximal opening of the outer lumen;
coupling the first extension tube to the inner lumen using a first pin, and coupling the second extension tube to the second passageway using a second pin; and
molding a hub over the insert, a proximal section of the outer lumen, and a distal section of both the first and second extension tubes.

13. The method according to claim 12, further comprising the steps of removing the first pin to establish fluid communication between the first extension tube and inner lumen, and removing the second pin to establish fluid communication between the second extension tube and outer lumen.

14. The method according to claim 12, wherein the insert further comprises a shoulder near the distal end, the inserting step further comprising bringing the shoulder in abutting relationship with a wall of the outer lumen defining the outer lumen proximal opening.

15. The method according to claim 12, wherein the molding step comprises molding the hub over the insert so that the hub completely encapsulates the insert.

* * * * *